United States Patent [19]

Wu

[11] Patent Number: 4,501,674

[45] Date of Patent: Feb. 26, 1985

[54] METHOD FOR REDUCING CORROSIVENESS OF AQUEOUS FLUIDS

[75] Inventor: Yulin Wu, Bartlesville, Okla.

[73] Assignee: Phillips Petroleum Company, Bartlesville, Okla.

[21] Appl. No.: 413,647

[22] Filed: Sep. 1, 1982

[51] Int. Cl.³ ............................................. C23F 11/14
[52] U.S. Cl. ............................ 252/8.55 D; 166/244 R; 166/244 C; 252/392; 422/14
[58] Field of Search ....................... 252/8.55, 387, 388, 252/389 R, 392; 166/244 R, 244 C

[56] References Cited

U.S. PATENT DOCUMENTS

| Re. 23,523 | 7/1952 | Baker | 99/48 |
|---|---|---|---|
| 3,160,508 | 12/1964 | Scott | 99/182 |
| 3,288,211 | 11/1966 | Johnston | 166/9 |
| 3,625,888 | 12/1971 | Redmore et al. | 252/8.55 D |
| 3,684,710 | 8/1972 | Cayle et al. | 252/8.55 R |
| 3,770,055 | 11/1973 | Larsen | 252/8.55 D |
| 4,059,533 | 11/1977 | Watson et al. | 252/8.5 A |
| 4,231,869 | 11/1980 | Carlberg et al. | 166/244 C |
| 4,238,349 | 12/1980 | Larsen et al. | 252/8.55 D |
| 4,238,350 | 12/1980 | Larsen et al. | 252/8.55 D |
| 4,240,438 | 12/1980 | Updike et al. | 128/635 |
| 4,329,448 | 5/1982 | Cox et al. | 252/8.55 R |
| 4,339,349 | 7/1982 | Martin et al. | 252/8.55 D |
| 4,401,122 | 8/1983 | Clark | 128/632 |

*Primary Examiner*—Ben R. Padgett
*Assistant Examiner*—T. J. Wallen

[57] ABSTRACT

A method is provided for reducing the corrosiveness of an aqueous fluid, particularly water containing dissolved oxygen and corrosive chemical agents such as naturally-occurring brine. According to the method, an enzyme which reacts with a substrate and consumes oxygen is added to the water along with a suitable substrate. Crude oil or other hydrocarbon material is also added to the water. The resulting water is less corrosive than water not containing the described system. In another embodiment of the invention, a water-flood method of post-primary oil recovery is provided in which the brine used is made less corrosive to metal drilling equipment by the addition to the water of an oxygen-consuming enzyme, a suitable substrate for the enzyme, and crude oil or other hydrocarbon material.

26 Claims, No Drawings

METHOD FOR REDUCING CORROSIVENESS OF AQUEOUS FLUIDS

BACKGROUND

The invention relates to the reduction of the corrosiveness of oxygen-containing water. It further relates to post-primary oil recovery processes involving the introduction of water into an underground formation.

In certain large-scale uses of water for industrial purposes, it is economically necessary to use naturally-occurring water near the site of the application. Such naturally-occurring water will often contain high concentrations of salts and dissolved oxygen. Such highly-oxygenated water is corrosive to any metal equipment with which it comes in contact, adding significantly to the expense of the process.

An example of such a process is the post-primary recovery of oil using various water-flooding procedures. The large quantities of water involved make it necessary to use naturally-occurring brine, the high salt content of which makes it corrosive to the down-well metal drilling equipment. The problem of corrosion is particularly great in off-shore oil drilling sites, where the sea water employed for flooding the formation is highly corrosive.

Oxygen-consuming enzyme systems can be used to deoxygenate such water and reduce its corrosiveness. For example, alcohol oxidase enzymes, which catalyze the reaction of an alcohol with oxygen to produce an aldehyde and hydrogen peroxide, can be added to oxygen-containing water in combination with a suitable alcohol substrate to reduce the oxygen content of the water. It has been found that the reduction of the oxygen content of highly-saline water is not adequate for some purposes to sufficiently reduce corrosion, possibly because of the production of by-products which are themselves corrosive.

It would be desirable to reduce the corrosiveness of brine by deoxygenaton to a sufficient extent to render the brine useful for a variety of purposes in which the brine comes in contact with corrodible surfaces.

It is therefore an object of the present invention to provide a method for reducing the corrosiveness of aqueous fluids used in processes in which the fluids come in contact with corrodible surfaces.

It is a further object to reduce the oxygen content of brine.

it is a further object to provide an improved method of post-primary oil recovery in off-shore oil wells.

SUMMARY OF THE INVENTION

According to the invention, the corrosiveness of an aqueous fluid such as oxygen-containing brine is reduced by contacting the aqueous fluid with a composition comprising an enzyme which catalyzes an oxygen-consuming reaction, a suitable substrate for the enzyme, and a hydrocarbon material. The method is particularly suited to the deoxygenation of brine used in post-primary oil recovery processes prior to the injection of the brine into an oil-containing formation. The use of a hydrocarbon in combination with the enzyme/substrate system has been found to significantly reduce the corrosiveness of the brine.

DETAILED DESCRIPTION OF THE INVENTION

Naturally-occurring brine can contain, depending upon the temperature and pressure of its location, large amounts of dissolved oxygen. Water in the North Sea would typically contain about 12 mg/l dissolved oxygen in addition to the large concentration of salts.

Enzyme substrates suitable for use in the invention include alcohols which are substrates for alcohol oxidase enzymes. These include lower alkanols such as methanol, ethanol, propanol and butanol.

the enzymes suitable for the method are those which catalyze the reaction of a substrate with oxygen, such as alcohol oxidases, which catalyze the following reaction:

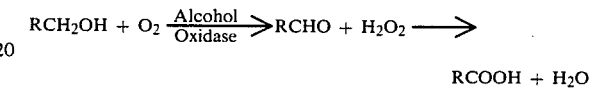

in which R is selected from hdyrogen, methyl, ethyl and propyl.

Thus, according to the reaction scheme above, an alcohol oxidase enzyme catalyzes the removal of oxygen in the presence of, e.g., methanol or ethanol to produce, respectively, formaldehyde or acetaldehyde and hydrogen peroxide. Under appropriate conditions, the aldehyde is further oxidized to carboxylic acid. The enzyme is not consumed by the reaction but functions continuously so long as oxygen and aqueous alcohol are both present.

The enzyme catalase is contained in alcohol oxidase preparations derived from single-cell protein productions, except high-purity alcohol oxidase preparations refined by dialysis. For enzyme preparations containing catalase, the following catalytic reaction will also occur:

The oxygen produced in this reaction will be consumed in the alcohol oxidase-catalyzed reaction. Catalase can thus also be present in the invention deoxygenation system if desired to reduce the amount of $H_2O_2$ present.

It has been found that the use of crude oil or other hydrocarbon material with the oxidase/alcohol deoxygenation system has the effect of at least partially overcoming the corrosive effects of the aldehyde, hydrogen peroxide and carboxylic acid products of the oxygen-consuming reaction.

The enzyme can be used in the form of (1) whole cell suspensions, (2) ruptured cell homogenates, (3) cell-free supernatants or (4) in purified form. The form used for a given application will depend at least in part upon the plugging, of either equipment or formation, which may occur with the use of (1) or (2).

The alcohol oxidase enzyme can be immobilized on an inert support so that enzymes are not added to the water but catalyze oxygen removal as the water containing dissolved oxygen and alcohol passes in contact with the immobilized enzymes.

Suitable microorganisms which can be cultured on an aqueous methanol-containing substrate and thus provide a source of alcohol oxidase include the following: *Gliocladium deliquescens, Paecilomyces varioti, Tri-* choderma lignorum, Candida boidinii, Candida methanolica, Candida parapsilosis, Hansenula capsulata, Hansenula glycozyma, Hansenula henricii, Hansenula minuta, Hansenula nonfermentans, Hansenula philodendra, Hansenula polymorpha, Hansenula wickerhamii, Kloeckera species, Pichia haplophila, Pichia lindnerii, Pichia pastoris, Pichia pinus, Pichia trehalophila, Torulopsis glabrata, Torulopsis pinus, Torulopsis methanodomerquiii, Torulopsis methanolovescens, Torulopsis methanosorbosa, Torulopsis nitratophila and the like. The particularly preferred alcohol oxidases are recovered from cells of Hansenula polymorpha and Pichia pastoris.

The presently preferred alcohol oxidase is obtained from methanol utilizing Pichia-type microorganisms comprising microorganisms of genus Pichia and microorganisms genetically and/or taxonomically closely related to Pichia. Specific examples of such methanol-utilizing Pichia yeast include: Pichia pastoris, Pichia pinus, Pichia trehalophilya, and Pichia molischiana.

Alcohol oxidase can be obtained commercially from chemical and biological supply houses. However, in a preferred embodiment the alcohol oxidase is obtained from fermentation of an alcohol by a selected microorganism followed by separation of the alcohol oxidase.

An alcohol oxidase can be isolated from Pichia pastoris in soluble form, or crystallized to purity, using a dialysis precipitation procedure. The enzyme is isolated from a suspension of cells taken from a fermenter by homogenizing in a Dynomill glass-bead mill and separating the resultant supernatant containing the alcohol oxidase from the cellular debris by centrifugation. This supernatant, which contains 200–300 enzyme units (Eu) per mL, can be further treated by adjusting the pH to 6.5 and dialyzing against 10 volumes of water. When the molar ionic strength of the crude enzyme solution decreases to about 0.02 M sodium phosphate, a precipitate of the alcohol oxidase forms.

The supernatant with relatively high enzymatic activity (200–300 Eu/mL) also contains large amounts of catalase, an enzyme which rapidly dismutates two moles of hydrogen peroxide into one mole of oxygen gas and two moles of water. Thus, alcohol oxidase is obtainable from Pichia pastoris in various degrees of purity:
(a) Whole single cell protein suspension: Both alcohol oxidase and catalase enzymes are available over long time periods by diffusion through cell walls.
(b) Homogenate of ruptured cells: Both alcohol oxidase and catalase enzymes are available in solution with significant amounts of cellular debris.
(c) Supernatant after centrifugation of (b): The cell-free supernatant contains relatively high enzymatic activity (200–300 Eu/mL) comprising alcohol oxidase and catalase.
(d) High purity alcohol oxidase by dialysis of (c): The precipitated alcohol oxidase of about 95% purity accounts for over 80% of the enzymatic activity of the above supernatant.

Broadly, according to a preferred method of preparing the alcohol oxidase, an aqueous suspension of cells having alcohol oxidase activity is prepared by fermentation of methanol as carbon energy substrate using a methanol-utilizing microorganism. The aqueous suspension of cells can be homogenized to produce a homogenate having alcohol oxidase activity.

Suspended solids can be removed from such a homogenate by centrifugation, filtration, or the like, and the resulting supernatant or cell-free fluid can be used as a crude solution having alcohol oxidase activity.

A crystalline, electrophoretically pure alcohol oxidase can be further prepared from the crude solution by ultrafiltration or dialysis or by other suitable means, presently preferably and conveniently by dialysis.

In a number of applications wherein $H_2O_2$ by-product is undesirable, the enzyme catalase can also be present in the enzyme treatment of aqueous fluid which contain free oxygen. The net result of the reactions catalyzed by the enzyme combination of alcohol oxidase and catalase is the scavenging of free oxygen and the conversion of the by-product $H_2O_2$ into water.

The enzyme-catalyzed deoxygenation systems described herein are operable over a pH range of 6 to 9 with an optimum pH range of 6.5 to 7.5. A temperature range of 0° to 60° C. is suitable with an optimum temperature range of about 40° to 50° C. The enzyme preparations can be stored indefinitely at 0° C. without any appreciable loss of activity. The catalytic enzymes of the subject deoxygenaton systems are active over a salinity range of 500 ppm total dissolved solids (TDS) to about 300,000 ppm TDS. In regard to stabilizers, 100 to 500 ppm formaldehyde or about 0.02 weight percent sodium azide is effective in maintaining a high level of enzyme activity in solution within the designated ranges of pH and temperature.

Two presently preferred strains of suitable yeasts of the species Pichia pastoris have been deposited with the U.S. Department of Agriculture, Agriculture Research Service, Northern Regional Research Laboratories of Peoria, Ill., and have received the numerical designations NRRL Y-11430 and Y-11431.

In the fermentation process, a species of methanol competent Pichia-type yeast is cultured under aerobic aqueous fermentation conditions using methanol as the carbon energy source. Preferably the methanol is supplied under conditions so that methanol is the growth-limiting factor. The methanol-limiting conditions are defined as a concentration of methanol which is the minimum concentration of methanol which results in a maximum growth rate for a given set of fermentation culture conditions. Preferably, the fermentation is conducted under high-cell density conditions, i.e., so that cell density is 50, more preferably 100, grams or greater on a dry weight basis per liter of ferment (cells plus aqueous liquor). The selected yeast is grown in a batch or continuous process in the presence of oxygen, methanol, and an assimilable source of nitrogen. Various types of fermentation processes and apparatuses known in the art can be utilized. For example, a foam-type fermenter such as described in U.S. Pat. No. 3,982,998, or other suitable fermenter can be used.

The needed oxygen can be supplied to the fermenter as such, or in the form of air or oxygen-enriched air, in a range of pressures from such as about 0.1 atm. to 100 atm., as is known in the art.

Fermentation pressures are generally within the range of about 0.1 to 100 atmospheres, more usually about 1 to 30 atmospheres, and more preferably about 1 to 5 atmospheres since the higher pressures result in a higher level of dissolved oxygen in the aqueous medium and usually higher cell productivities.

The assimilable nitrogen source for the fermentation can be any organic or inorganic nitrogen-containing compound which provides nitrogen in a form suitable for metabolic utilization by the microorganisms, such as proteins, amino acids, urea, and the like; and ammonia, ammonium hydroxide, ammonium nitrate, and the like. The presently preferred nitrogen sources include ammonia and ammonium hydroxide for convenience and availability.

The growth of the microorganism is sensitive to the operating temperature of the ferment. Each particular strain of microorganism has an optimum temperature for growth. Exemplary fermentation temperatures are in the range of about 20° C. to about 65° C.

The pH range in the aqueous microbial ferment usually is controlled in the range of about 3 to 7, usually about 3.5 to 5.5, by suitable additions of acidic or alkaline material. Preferences of particular species of microorganisms for a particular pH range are dependent to some extent on the medium employed, as well as on the particular microorganism, and thus may vary somewhat with change in medium as can be readily determined by those skilled in the art.

For isolation of the alcohol oxidase enzyme, fluid is prepared which is an aqueou suspension containing cells of the selected microorganism. The aqueous fluid can be fermenter effluent which can be used as is, or preferably after adjusting the pH as described below. Alternatively, the suspended microorganism cells can be initially separated from the fermentation medium, for example, by centrifugation or by filtration through filters having a pore size less than the size of the individual cells, and subsequently resuspended in a convenient volume of water or of an appropriate aqueous buffer, for example $KH_2PO_4/Na_2HPO_4$ buffer at 0.2 M. The cell density in the aqueous suspension must be greater than a minimum crystallization density. Satisfactory results are obtained if the fluid cell density is greater than about 75 grams on a dry weight basis per liter of fluids. If the fermenter effluent is to be used as the fluid, it should be first adjusted to a pH of such as about 7.5 by addition of a base such as ammonium hydroxide, sodium hydroxide, and the like, for most satisfactory results. The pH is not believed to be critical, and the pH of the aqueous suspension need not be adjusted prior to homogenization. It is preferable to adjust the pH broadly in the range of about 6–9 since in this range the enzyme is active and stable.

The cell-containing fluid can be homogenized by suitable means known to the art. The homogenate solids are separated from the homogenate to produce a crude solution containing the alcohol oxidase as a soluble component. For example, the homogenate solids can be removed by centrifugation to yield a cell-free supernatant. Alternatively, the solids can be removed by filtration through filters having a suitable pore size, followed by pH adjustment, if desired, for optimum activity. If further purification is desired, such as recovery of crystalline alcohol oxidase, the pH can be adjusted to the range of 5.75 to 6.75 preferably to pH 6.5.

The crude solution containing the soluble alcohol oxidase can be treated to recover crystalline alcohol oxidase either in more concentrated solid form such as by fractional precipitation with ammonium sulfate, or and preferably as the crystalline form exhibiting highest activity by treatment under dialysis conditions either by conventional dialysis modes or by applying ultra-filtration to increase the rate of recovery.

In dialysis, the alcohol oxidase containing solution is dialyzed against a dialysis medium, for example water or a buffer solution, to achieve a recovery range solution on the enzyme side of the membrane having an ionic strength in a recovery range of between 0.05 M and 0.01 M thereby effecting precipitation of an electrophoretically homogeneous crystalline oxidase. Satisfactory crystallization has been observed where the effective cell density is about 75 grams (on a dry weight basis) per liter of aqueous fluid. Crystallization occurs at even lower effective cell densities although the amount of crystalline alcohol oxidase recovered is less.

During dialysis, the pH of the alcohol oxidase containing solution should be maintained in the range of about 5.75 to about 6.75 by use of a suitable buffer system such as potassium dihydrogen phosphate and disodium hydrogen phosphate. Preferably the pH range is from about 6.0 to 6.5 for recovery of maximum amounts of crystalline alcohol oxidase.

The dialysis can be safely carried out at temperatures in the range of from about 4° C. to 40° C. Sufficient time, generally more than one hour, and preferably 18 hours or more, is needed for crystallization to occur.

At the end of the dialysis, the alcohol oxidase is present in the dialysis bag as a crystalline solid. The crystalline alcohol oxidase can be readily separated from the dialysis medium, such as by decanting the liquid in the dialysis bag from the solid crystals. The moist crystals can be further processed as desired for storage. For example, the crystal slurry can be frozen followed by lyophilization to form a dry powder, or can be dissolved in water or more preferably in a phosphate buffer. The alcohol oxidase can be stored frozen without significant loss of enzymatic activity. Stabilizer compounds known to stabilize enzyme solutions against denaturation and loss of enzymatic activity can be added, such as sucrose or glycerol, or 0.02 weight % sodium azide.

It is suitable to store the prepared enzyme at temperatures in the range of about 4° C. to 40° C. Only minimal loss of activity occurs on storage of the enzyme at 4° C. in 0.1 M phosphate buffer at pH 7.5, and with such as about 0.2% sodium azide to inhibit microorganism growth.

The foregoing detailed description of a particular alcohol oxidase enzyme is directed to the presently-preferred form of enzyme for the invention method and is not intended to be limiting. Any enzyme which catalyzes the reaction between a substrate material and oxygen is suitable for the invention method.

The addition of a hydrocarbon to the enzyme/substrate system improves the corrosion-reducing capabilities of the system. It is theorized that this effect is the result of the movement of potentially-corrosive aldehyde, hydrogen peroxide and carboxylic acid products of the reaction into the organic phase provided by the added hydrocarbon. Any hydrocarbon which can provide an organic phase in the treated water can be used in the invention method, including aromatic compounds and saturated and unsaturated aliphatic compounds. Such hydrocarbons include but are not limited to xylene, benzene, toluene, hexane, decane, butane, fuel oil, cumene, tetralin, diesel, hexadecene, extract oils, petroleum fractions and crude oil. Glycerides of unsaturated fatty acids such as tung oil, cottonseed oil, linseed oil, soybean oil and the like can also be used alone or in combination with one or more of the above cited hydrocarbons. The presently-preferred hydrocarbon for this purpose, because of its availability at the site of the primary application of the deoxygenation system and its effectiveness, is crude oil.

The crude oil or other hydrocarbons can be added to the deoxygenation system in any amount effective for reducing the corrosiveness of the aqueous system. The crude oil can generally be added in the amount within the range of about 0.1 to about 50 volume percent, preferably about 0.5 to about 30, most preferably about 2 to about 20 volume percent, based on the volume of water treated.

The components of the deoxygenation system can be added to the oxygen-containing water in any order but the preferred manner of mixing the components is adding methanol to the oxygen-containing water, then adding the alcohol oxidase and finally adding the crude oil. Preferably, the components are added with mixing or agitation of the water. The water containing the deoxygenation system can, if desired for more complete oxygen removal, be held prior to use for a period of time which depends upon the extent of oxygen removal desired and the conditions. Generally, a time of up to six hours will be sufficient to remove 50% of the oxygen, and 90% removal would be achieved within 24 hours.

The alcohol oxidase is present in an amount sufficient to catalyze the oxidation reaction. The enzyme will generally be present in an amount of at least about 0.01 E.U. per mL of treated water to whatever level may be economically feasible. The alcohol amount can be as low as 20 ppm to any higher practical limit. Generally, the enzyme concentration will range from about 0.01 to about 100, preferably about 0.1 to 1.0 enzyme units per mL of water being treated. Generally, the alcohol concentration will range from about 0.8 to about 10,000 moles alcohol per moles of dissolved oxygen, preferably about 1 to about 1,000 moles per mole of oxygen.

The oxygen-containing water thus treated for removal of the oxygen can be used for whatever ultimate purpose is desired. For example, brine treated according to the invention method can be used in post-primary methods of oil recovery involving water-flooding techniques. The thus-treated brine will be less corrosive to the downhole metal drilling equipment than untreated brine.

In the post-primary oil recovery methods using deoxygenated brines, the preferred technique includes adding alcohol oxidase and the substrate alcohol to the brine, contacting the thus-treated brine with crude oil, and subsequently introducing the brine into the oil-bearing reservoir through an injection well. The treated water is then used to drive reservoir oil toward production wells.

EXAMPLE

Runs were performed to assess the effectiveness of an alcohol oxidase/methanol system as a corrosion inhibitor in oxygen-saturated brine. The brine formulation was designed to simulate water from the Ekofisk oil field in the North Sea. A 1000 mL sample of synthetic Ekofisk water (93.1 g $CaCl_2 \cdot H_2O$, 46.4 g $MgCl_2 \cdot 6H_2O$ and 781.1 g NaCl per 5 gal. distilled $H_2O$) was saturated with oxygen for 30 minutes. Absolute methanol (10 mL) and alcohol oxidase from *Pichia pastoris* (3 mL of a cell-free supernatant containing 200–300 e.u. per mL of supernatant from Phillips Petroleum Company) were added to the brine. The reactor was sealed. An ionization probe in combination with a Magma Corrator was used to measure corrosion rate. The results are shown in Table I.

TABLE I

| Run No. | Alcohol Oxidase (mL) | Methanol (mL) | Additive | Water (mL) | Corrosion Rate MPY | Pitting Index |
|---|---|---|---|---|---|---|
| 1 | None | None | None | 1000 | 35 | 11 |
| 2 | 3.0 | 10 | None | 1000 | 8.5 | 4.0 |
| 3 | 3.0 | 10 | None | 1000 | 11.0 | 5.0 |
| 4 | 3.0 | 10 | (2 mL) | 1000 | 29 | 3.0 |
| 5 | 3.0 | 10 | $(C_2H_5)_2NH$ (0.2 mL) | 1000 | 17 | 11 |
| 6 | 3.0 | 10 | Crude Oil (100 mL) | 900 | 2.1 | 0.7 |
| 7 | None | None | Crude Oil (100 mL) | 900 | 13 | 2.5 |

Control run 1 illustrates the corrosiveness of oxygen-saturated synthetic Ekofisk brine. Control run 7 employing crude oil alone resulted in a lower corrosion rate. Runs 2 and 3 demonstrate that alcohol oxidase and methanol used in combination further reduced corrosion but not as effectively as invention run 6. Runs 4 and 5 illustrate that the addition of reducing agents such as formaldehyde and diethylamine to the alcohol oxidase/methanol system gave a modest reduction in the corrosion rate. Invention run 6 shows the significant improvement in corrosion reduction achieved by the enzyme system when used in combination with crude oil additive.

I claim:

1. A method for reducing the corrosiveness of an oxygen-containing aqueous fluid, the method comprising contacting the aqueous fluid with a deoxygenating system comprising (a) an enzyme which catalyzes the reaction between a substrate material and oxygen, (b) the substrate material and (c) at least one hydrocarbon.

2. The method of claim 1 in which the enzyme is an alcohol oxidase enzyme.

3. The method of claim 2 in which the substrate material is an alkanol.

4. The method of claim 3 in which the alkanol is selected from methanol, ethanol, propanol and butanol.

5. The method of claim 4 in which the hydrocarbon is selected from crude oil, petroleum fractions, xylene, benzene, toluene, hexane, decane, butane, fuel oil, diesel and hexadecene.

6. The method of claim 4 in which the alcohol oxidase enzyme is derived from a microorganism of genus Pichia.

7. The method of claim 2 in which sufficient enzyme is present such that enzyme activity is present in an amount of at least about 0.01 E.U. per mL of treated aqueous fluid, the substrate material is present in an amount of at least about 20 ppm per mL of treated aqueous fluid and the hydrocarbon is present within the range of about 0.1 to about 50 volume percent, based on the amount of aqueous fluid.

8. The method of claim 7 in which the enzyme is an alcohol oxidase enzyme, the substrate material selected from methanol and ethanol, and the hydrocarbon is crude oil.

9. The method of claim 8 in which the aqueous fluid is contacted by the enzyme by passing the aqueous fluid across the enzyme immobilized on an inert support.

10. The method of claim 8 in which the aqueous fluid is brine.

11. The method of claim 1 in which the hydrocarbon is present within the range of about 2 to about 20 volume percent, based on the amount of water.

12. In an oil recovery method in which an aqueous fluid is introduced into an oil-bearing reservoir via a metal conduit, the improvement comprising introducing into the oil-bearing reservoir aqueous fluid which has been treated by a method comprising:

contacting the oxygen-containing aqueous fluid with a deoxygenation system comprising (a) an enzyme which catalyzes the reaction between a substrate material and oxygen, (b) the substrate materal and (c) at least one hydrocarbon.

13. The method of claim 12 in which the aqueous fluid is introduced into the reservoir via an injection well.

14. The method of claim 12 in which the aqueous fluid is introduced into the reservoir via an injection well as part of a waterflood oil recovery technique.

15. The method of claim 12 in which the enzyme is an alcohol oxidase enzyme and the substrate is selected from methanol, ethanol, propanol and butanol.

16. The method of claim 15 in which the hydrocarbon is selected from crude oil, petroleum fractions, xylene, benzene, toluene, hexane, decane, butane, fuel oil, diesel and hexadecene.

17. The method of claim 16 in which the hydrocarbon is crude oil.

18. The method of claim 17 in which the alcohol oxidase is derived from a microorganism of genus Pichia and the substrate is methanol.

19. The method of claim 18 in which the crude oil is present in an amount sufficient to solubilize any aldehyde and hydrogen peroxide produced from deoxygenation of the oxygen-containing aqueous fluid.

20. The method of claim 19 in which the aqueous fluid is contacted by tne enzyme by passing the aqueous fluid across the enzyme immobilized on an inert support.

21. The method of claim 19 which further comprises driving the aqueous fluid through the reservoir toward a production well.

22. The method of claim 12 in which the hydrocarbon is present in an amount sufficient to reduce the corrosiveness of the aqueous fluid.

23. A composition for deoxygenating oxygen-containing water comprising (a) an enzyme which catalyzes the reaction between a substrate material and oxygen, (b) the substrate material, and (c) a hydrocarbon selected from the group consisting of crude oil, petroleum fractions, xylene, benzene, toluene, hexane, decane, butane, fuel oil, diesel and hexadecene.

24. The composition of claim 23 in which the hydrocarbon is crude oil.

25. The composition of claim 23 in which sufficient enzyme is present such that enzyme activity is within the range of at least about 0.1 to about 1.0 e.u. per mL of treated water, the substrate material is present in an amount within the range of about 1 to about 10,000 moles per mole of dissolved oxygen and the hydrocarbon is present within the range of about 2 to about 20 volume percent, based on the amount of water.

26. The composition of claim 23 in which the hydrocarbon is selected from the group consisting of crude oil, petroleum fractions, xylene, benzene, toluene, hexane, decane, butane, fuel oil, diesel and hexadecene.

* * * * *